(12) United States Patent
Lamming

(10) Patent No.: US 6,602,676 B1
(45) Date of Patent: Aug. 5, 2003

(54) TESTING METHOD

(75) Inventor: G. Eric Lamming, Melton Mowbray (GB)

(73) Assignees: Milk Development Council (GB); University of Nottingham (GB)

(*) Notice: Subject to any disclaimer, the term of this patent is extended or adjusted under 35 U.S.C. 154(b) by 0 days.

(21) Appl. No.: 09/544,686

(22) Filed: Apr. 7, 2000

Related U.S. Application Data

(60) Provisional application No. 60/128,586, filed on Apr. 9, 1999.

(51) Int. Cl.[7] .............................................. G01N 33/543
(52) U.S. Cl. ...................... 435/7.92; 435/7.1; 435/7.93; 435/7.94; 435/806; 436/504; 436/814
(58) Field of Search .................................. 435/7.1, 7.94, 435/7.93, 806, 7.92; 436/504, 814

(56) References Cited

FOREIGN PATENT DOCUMENTS

| EP | 0282192 A1 | 9/1988 |
|---|---|---|
| GB | 2120785 A | 12/1983 |

OTHER PUBLICATIONS

Sianangama et al., Theriogenology. vol. 38, No. 1, pp. 85–96. 1992.*
Starbuck et al., Cattle Pract. vol. 7, Part 4, pp. 397–399. 1999.*
Walton et al., Can. J. Vet. Res., vol. 54, No. 3, pp. 305–308. 1990.*

* cited by examiner

*Primary Examiner*—Bao-Thuy L. Nguyen
(74) *Attorney, Agent, or Firm*—Nixon Peabody LLP

(57) ABSTRACT

This invention relates to a method of predicting pregnancy, particularly, in a cow, the method comprising taking a milk sample from the cow in which a milk progesterone concentration of >3 ng ml$^{-1}$ by Day 4 post insemination is indicative that the animal is pregnant. The invention also relates to methods of improving pregnancy success by timely supply of progesterone or a functional equivalent thereof (progestagen); to methods of assessing suitability for progesterone replacement therapy; and to methods of embryo transfer.

15 Claims, 4 Drawing Sheets

REGRESSION OF PREGNANCY RATE ON THE MEAN PROGESTERONE CONCENTRATION ON DAY 24 POST-INSEMINATION IN HOLSTEIN-FRIESIAN COWS (n=1451). GOMERTZ RELATION MODEL WAS FITTED $y=ae^{-b-cx}$, $a=81.02$, $b=3.34$, $c=0.308$ ($r=0.985$, s.e.$=5.6$)

TESTING METHOD

This application claims the benefit of U.S. Provisional Application No.: Application No. 60/128,586 filing date Apr. 9, 1999.

This invention relates to a method of testing and is particularly though not exclusively concerned with a method of testing progesterone levels and pregnancy in cows.

Reproductive performance is one of the important factors determining the profitability of dairy herds. Ideally, the calving interval should average one year, but this can only be achieved if the pregnancy success and detection of oestrous rates are high and the interval between parturition and first service is less than 90 days (Bulma, D. C. and Lamming G. E. J Reprod. Fert (1978) 54: 447–58).

The basic physiology of pregnancy in cows is relatively well understood. Following ovulation, the release of an oocyte for fertilisation, which usually occurs 6–12 hours after the end of oestrous (occasionally up to 36 hours later), the rapidly growing corpus luteum (CL) is formed from follicular cells remaining in the ovary. One of the main functions of the CL is to secrete the steroid hormone progesterone ($P_4$). During a normal 21-day oestrous cycle an animal shows measurable $P_4$ levels between days 4–19 post oestrous and following the demise of the CL a period of 6 to 7 days with low $P_4$ concentrations.

The early embryo is dependent on adequate progesterone concentrations. Fertilised ova remain in the oviduct until day 4 post-ovulation, and then migrate to the uterus. The embryo remains free or loosely attached until about day 25 of pregnancy. Prior to implantation of the embryo in the uterine wall, embryos are supported solely by secretions that accumulate in the uterine lumen. Changes in timing and magnitude of peripheral progesterone concentrations affect the uterine environment which in tun affects embryo viability. Progesterone is believed to play a major role in controlling the maternal secretion of nutrients, growth factors and enzymes required for successful embryo development. In sheep, changes in the content of total protein and of several metabolic enzymes in ovine uterine flushings follow the growth and regression of the CL (Ashworth et al (1989) Animal Reprod. Sci. 21: 213–221). Although in the cow, Day 16 post insemination is often regarded as the period for the material recognition of pregnancy it is well established that important physiological communications must have occurred between the embryo and its mother before that date. It has previously been shown that milk progesterone concentrations are higher in pregnant than in mated non-pregnant cows between days 10 and 18 of pregnancy (Lamming et al (1989) J. Reprod. and Ferth. Suppl. 37: 245–252).

Artificial insemination (AI) of cows is often used in dairy herds due to the ease of use and relative success of the process compared to natural insemination.

Them is currently major concern about the causes and impact of the increase in subfertility observed in dairy herds. Recent data derived from analysis of progesterone ($P_4$) from both mild and close monitoring of a large number of cows in the UK, shows a decline in pregnancy rate to artificial insemination in untreated cows ranging from 65% in 1975 to 1982 compared to 44% in 1995 to 1999; a decline of approximately 1% per year (Darwash, A. O et al (1999a) Anim. Sci 68: 333–347; Royal M. D. et al (1999) Pro Br. Soc. Anim. Sci. (in press). Similar findings for the USA, using field records, have been reported all recently (Beam S. W. and W. R. Butler (1999). J. Reprod. Fertil. Suppl. 54 (in press). An increased rate of embryo loss is claimed to be a major component of the reduced reproductive efficiency. To quantify its extent, estimates show a fertilization rate of 89 to 100% (Bearden, H. J. et al (1956) J. Dairy Sci 39: 312–318; Diskin, M. G. and J. M. Sreenan (1980) J. Reprod. Fertil. 59: 463–468; Kidder, H. E. et as (1954) J. Dairy Sci. 37: 691–697) with the pregnancy rate falling to approximately 80% by Day 13 post insemination and to less than 60% by Day 19 to 20 post insemination (Peters, A. R. (1996). Anim. Breed Abstr. 64: 587–598; Screenan, J. M. and M. G. Diskin (1986) Embryo Mortality in Farm Animals, pp 1–11 Mamnus Nijhoff, Dordrecht). Consequently, early embryo loss by Day 16 (approximately 35%) and later embryo loss (approximately 10%) are of major concern. These losses have been observed particularly in cows showing atypical ovarian hormone patters before mating, which occurs in about 50% of animals (Lamming G. E. and A. O. Darwash (1998) Anim. Reprod. Sci. 52: 175–190). As a result, calving rates to AI in UK dairy herds are now generally less than 50% and in some herds below 40% (Darwash A. O. et al (1999a) Anim. Sci supra).

Currently, there is increasing interest in the importance of the magnitude and pattern of luteal $P_4$ secretion post ovulation for both oestrous cycle control and the establishment and maintenance of pregnancy. Monitoring of milk $P_4$ concentrations facilitates examination of the impact of luteal $P_4$ patterns on pregnancy rates.

Fertility is often suggested as a result of the "timely" availability of $P_4$ concentrations between days 4 to 10 post AI (Ahmad, N et al (1996) J. Anim. Sci. 74: 1943–1952; Albihin, A. H et al (1991) Anim. Reprod. Sci. 26: 193–210; Erb, R. E. et al (1976) Theriogenology 5: 227–242; Hansel, W. (1981) J. Reprod. and Fertil. Suppi. 30: 231–239; Lamming, G. E. et al (1989) J. Reprod and Fertil. Suppl. 37: 245–252; Lamming G. E and A. O Darwash (1995) Biol. of Reprod. 52: Suppl. 1, abstr 63; Larson, S. F. et al (1997) J. Dariy Sci. 80: 1288–1295; Maurer, R. R. and S. E. Echternkamp (1982) Theriogenology, 17: 11–22; Parkinson, T. J et al (1994) Theriogenology 41: 1115–1126). Using daily milk sampling, measurable concentrations of $P_4$ ($\geq 3$ ng/ml) were detected in individual cows on Days 4 to 6 post-oestus (Darwash, A. O et al (1998) Fertil. and Reprod. Grub, Germany, November 1997; Darwash, A. O et al (1999b) Anim Sci. (in press) which coincides with Days 3 to 4 or 5 to 6 post AI.

Although insuffcient circulating $P_4$ concentration has often been suggested as the cause of early embryonic mortality which contributes to lowered fertility, $P_4$ concentrations essential for embryo survival have hitherto been un-defined. The present inventors have previously shown that a delay of as little as one day in the availability of adequate progesterone concentration can induce a sub-optimal uterine environment which is deterimental to embryo survival and speculated that determining critical levels of $P_4$ after insemination may assist in developing a non-pregnancy test possibly as early as day 7 post AI (Dash A. O and Lamming G. E. J. Animal Breeding (1998) 2: 41–43). The lack of a definition for the most appropriate timing and magnitude of $P_4$ needed during early pregnancy, has tempted a practice of blanket $P_4$ supplementation at various periods post AI, with inconsistent pregnancy results. A degree of improvement in fertility was achieved using progesterone releasing devices, (PRID), (Robinson N. A. et al (1989) J. Dairy Sci 72: 202–207) or controlled internal drug release (CIDR) (Macmillian, K. L and A. J Peterson (1993) Anim. Reprod. Sci. 33: 1–25) but others recorded no effect using CIDR (Van Cleeff, J. et al (1991) Theriogenology 36: 795–807). In all previous studies, $P_4$ supplementation was carried out as a blanket treatment regardless of whether the cow actually required it or not. The inventors believe that the indiscriminate use of progesterone supplementation, in fact, is the reason for the discrepancies between the result of studes on $P_4$ supplementation described above. Blanket treatment in some animals which already produce adequate $P_4$ levels may result in higher than optimal $P_4$ levels shortly after service which are known to have a detrimental influence on embryo survival (Farin P. W and Farin C. E. (1994) Biology of Reproduction 52: Suppl. Abstr 15, 23).

Consequently, there is a clear need to define the precise requirement for luteal $P_4$ secretion afer insemination and the conditions under which $P_4$ supplementation is appropriate and effective.

Post insemination milk $P_4$ concentrations in relation to pregnancy rates were studied in postpartum Holstein Friesian cows. In a preliminary study, analysis of milk samples showed that one day delay in milk $P_4$ rise >3 ng/ml (mean ±se 5.15±0.27 v 4.08±0.16 days) was associated with pregnancy failure. Based on this result two further studies were completed involving $P_4$ analysis of milk samples taken on Days 0, 5 and 24. In Study I mean milk $P_4$ concentration on Day 0 was 1.96±0.10 ng/ml (n=1451). Pregnancy rates were significantly correlated with Day 0 milk $P_4$ concentrations (r=−0.91) ranging between 51.3% at milk P4<3 ng/ml to 11.3% at >5 ng/ml. Milk $P_4$ concentration on Day 5 after insemination was 5.93±0.10 ng/ml. Pregnancy rat was 31.1% in 256 animals (17.6%) with post insemination luteal $P_4$ insufficiency ($P_4$ concentrations <3 ng/ml) compared with 52.4% for animals with 3 to 9 ng/ml and there was a highly significant effect of parity (10.2% incidence first lactation rising to 29.5% by third lactation). On Day 24, the mean miLk $P_4$ concentration was 15.98±0.32 ng/ml. Predicting pregnancy from Day 24 milk $P_4$ concentrations was accurate above 16 ng/ml and varied between 27.3% in animals inseminated at an inappropriate time in relation to ovulation compared to 83.3% for animals with low Day 0 (<3 ng/ml) and adequate $P_4$ concentrations on Day 5 (>3 ng/ml).

In Study II $P_4$ supplementation of cows with <3 ng/ml $P_4$ on Day 5 significantly increased pregnancy rates (from 28.9 to 57.9%) where pretreatment concentrations were between 1 and 2 ng/ml but not in animals above or below this range.

Data on milk $P_4$ concentrations on the day of insemination and on Days 5 and 24 thereafter provides valuable information on the potential fertility status of cows. Milk $P_4$ levels on Day 5 can be used to select suitable animals for $P_4$ supplementation to improve pregnancy rates. Luteal $P_4$ insufficiency on Day 5 may be used as an early test for non-pregnancy.

According to one aspect of the invention there is provided a method of predicting pregnancy in an inseminated cow, the method comprising taking a milk sample from the cow in which a milk progesterone concentration of >3 ng/ml by at least Day 4 post insemination is indicative that the animal is pregnant.

The method is non invasive and advantageous in that the milk samples can be readily obtained from the animal during the normal milking routine, being taken for example by the farmer.

According to another aspect of the invention, there is provided a method of improving pregnancy success in cows, the method comprising analysing milk progesterone levels from a cow and supplying the cow with progesterone, or a functional equivalent thereof if the milk progosterono level is <3 ng/ml$^{-1}$, and where the progesterone levels are measured from at least one of Day 4, 5 and 6 post insemination.

Using this method, the likelihood of a successful pregnancy can be improved without the use of blanket administration of progesterone or suitable progestagen, i.e. a compound having equivalent effects, particularly biological effects, to progesterone. In this way, indiscriminate use of hormones can be avoided.

According to another aspect of the invention, there is provided a method assessing a cow for suitability for progesterone replacement therapy, comprising assessing milk progesterone levels in the cow at least one of Day 4, Day 5 or 6 post insemination. Similarly using this method, the indiscriminate use of hormones can be avoided.

Embryo transfer in cattle is being used to a limited extent having been used on 1% of the total UK milk cow population in 1997 (24,000 recipients in 2.5 million cows. However, it is relatively expensive to perform. It is desirable to improve the success rate of embryo transfer.

According to another aspect of the invention, there is provided a method of embryo transfer in cows, the method comprising selecting as recipients for embyro transfer cows on the basis of milk progesterone levels taken on at least one of Day 4 to 6 post oestrous.

Methods in accordance with the invention wilt now be described, by way of example only, with reference to the accompanying drawings, FIGS. 1 to 4, in which.

Figure 1:
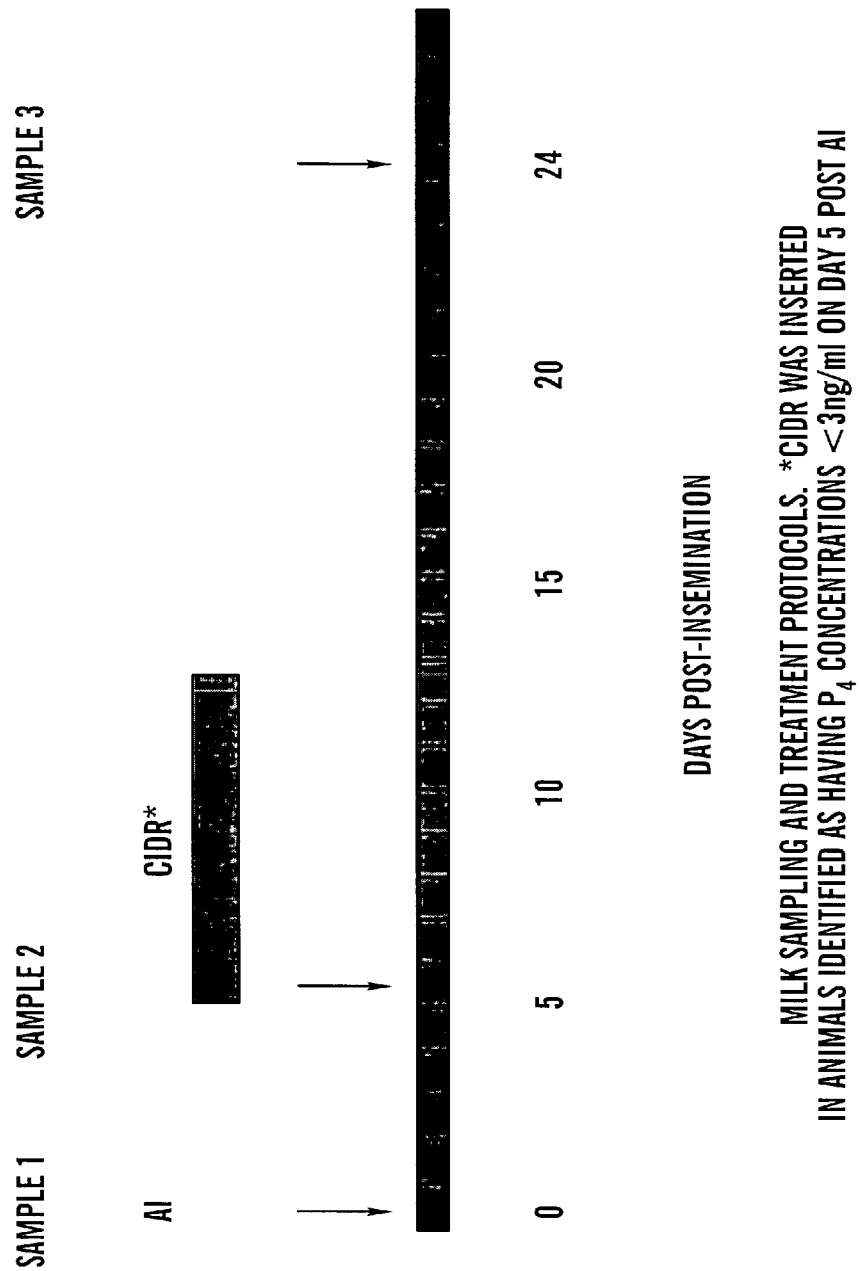
FIG. 1 illustrates the schedule of milk sampling and consequent supply by CIDR of progesterone according to a method in according with the invention.
Figure 2:
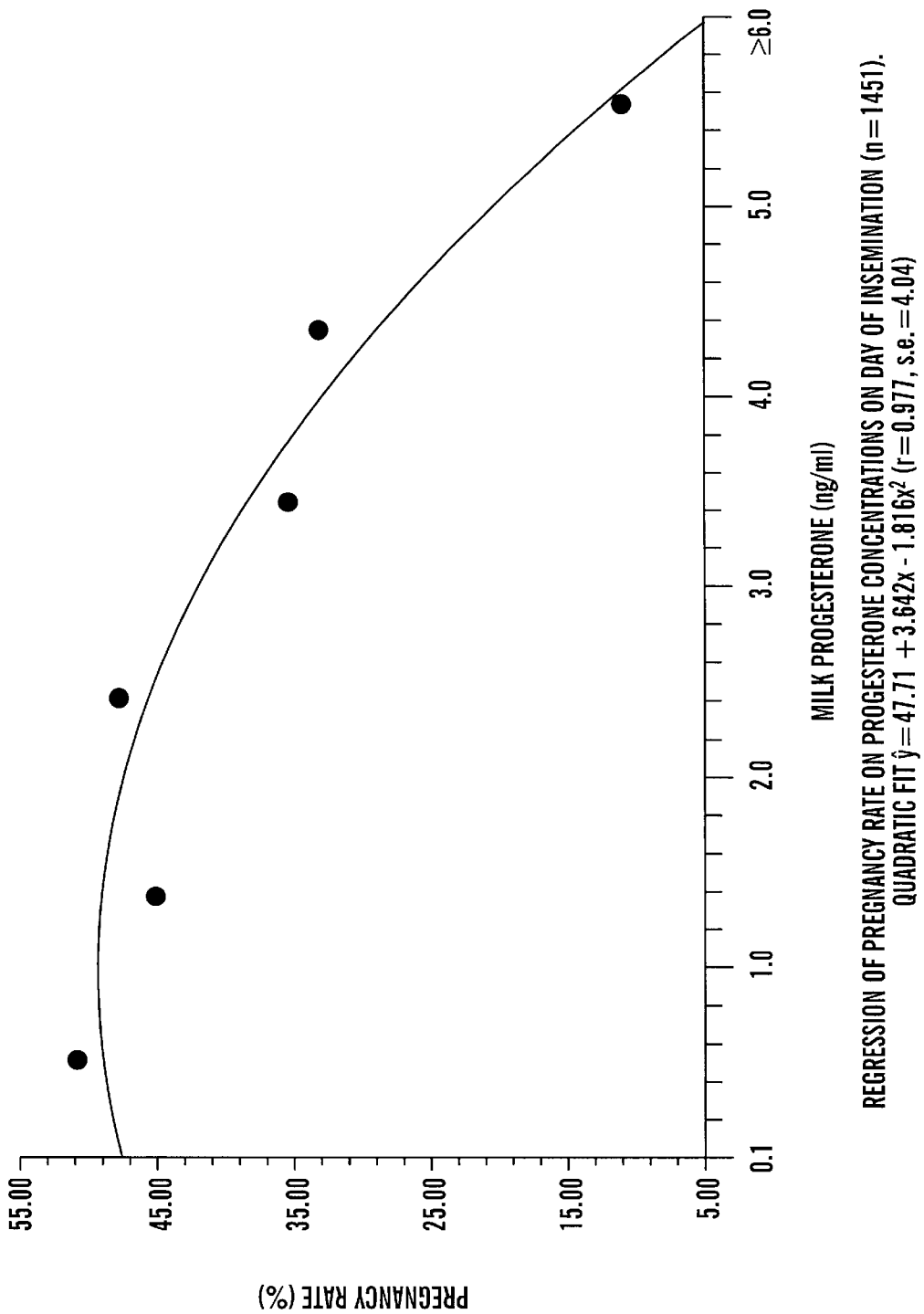
FIG. 2 illustrates a regression pregnancy rate on progesterone concentrations on Day of insemination.

Three experiments were completed. The results of a preliminary study involving daily sampling were obtained and following data analyses, two further studies (I&II) were carried out.

Experimental Animals and Sampling Protocols

Milk samples for $P_4$ assay and reproductive data were collected from British Friesian and Holstein-Friesian cows in seven commercial herds. The cows were housed in a free-stall system and fed rations to meet their production and maintenance requirements. Data on calving date, parity, AI date and pregnancy were recorded. For the preliminary study, milk samples were collected daily for $P_4$ determination from Day 7 postpartum until 100 days of the next gestation. The sampling protocol for animals in Studies I and II was limited to three milk samples per animal on Days 0, 5 and 24 post AI. The samples were placed in 30 ml plastic bottles, preserved using LACTAB III tablets (Thompson & Capper Ltd., Cheshire, England) and stored at 4° C. until they were assayed.

Milk Progesterone Assay

Milk $P_4$ concentrations in an un-extracted aliquot of whole milk were measured using either radio immunoassay (RIA) as described by Lamming and Bulman (Lamming, G. E. and D. C. Bulman (1976) Br. Vet. J. 132: 507–517) and Bulman and Lamming (Bulman D. C. and G. E. Lamming (1978) J. Reprod. Fertil. 54: 447–458) or enzyme linked immunosorbent assay (ELISA) kit (Ridgeway Science Ltd., Gloucestershire, UK) as illustrated by Darwash et al. (Darwash A. O et al (1999b) Anim Sci. (in press)). All samples and quality controls (QC) were assayed in duplicate and the mean value of both readings were used to indicate milk $P_4$ concentrations. The inta-and inter-assay coefficients of variation (CV) for the RIA method were 8.9% and 10.3%, respectively, with the limit of sensitivity, defined as twice the standard deviation of the blank values, was 0.38 ng/ml. for the ELISA method, based on QC values of 2 and 8 ng/ml, the intra-and inter-assay CV were 9.4 and 10.4. The lower and upper assay sensitivity were <1 and 23.5 ng/ml, respectively.

Furthermore, a routine laboratory procedure was adopted whereby all duplicate samples with milk $P_4$ values from 1.5 to 10.5 ng/ml were re-assayed until the CV of the duplicate was <15%.

Definitions

Timely Insemination

In most cows, oestrous is manifested between 48 and 72 hours following the regression of the corpus luteum (CL) when milk $P_4$ concentrations are usually low (<3 ng/ml). Since an abrupt rise (a blip) in $P_4$ concentration may occur in some animals on the Day of AI (Bulman, D. C. and G. E. Lamming (1979) Br. Vet. J. 135: 559–567; Dobson, H. et al (1975) Vet. Rec. 222–223), a single-day measurement may not give an accurate indication of the day after CL regression, when AI was performed. Therefore, in the present study milk $P_4$ concentrations on Days 0 and 5 post AI, were used to denote in each cow whether insemination had occurred at the appropriate time in relation to ovulation.

Pregnancy

The presence of an embryo or foetus determined by ultra sound scan or rectal palpation or the delivery of a calf was used to indicate whether a particular AI resulted in a confirmed pregnancy. Following determination of pregnancy, the accuracy of using milk $P_4$ concentrations on Day 24 post AI to predict pregnancy rates was calculated.

Preliminary Study

In order to investigate the timing and magnitude of spontaneously occurring luteinization post AI, $P_4$ concentrations in milk samples collected daily from the University of Nottingham dairy herd during 500 cycles were analysed. Cows identified as having cystic follicles or delayed luteolysis post AI which would affect the probability of pregnancy were excluded from the analysis. The outcome of 124 inseminations, where no hormonal therapy had been used 21 days previously, was characterized. Milk $P_4$ concessions were detennined in whole milk using RIA. The findings from this preliminary study formed the basis for farther investigations descnbed in Study I and II.

Luteal $P_4$ Insufficiency: The Choice of Day 5 Post AI

The results of the preliminary study using daily milk sampling revealed that pregnant animals had significantly (P<0.001) shorter intervals to milk $P_4$ rise ($\geq 2$ ng/ml) than animals which were not pregnant following timely AI (4.08d vs 5.15d). Consequently, a milk $P_4$ concentration of <3 ng/ml on Day 5 post AI was empirically chosen to indicate the advent of luteal $P_4$ insufficiency, resulting from either a delayed ovulation, development of an incompetent CL or both of these events.

Study I

A total of 1451 inseminations in 1228 untreated animals were included in this analysis. The levels of milk $P_4$ on Days 0, 5 and 24 post AI and their association with fertility were characterized. Progesterone concentrations on Day 0 and 5 were used to quantify the incidence of untimely AI in relation to ovulation and to assess the accuracy of predicting pregnancy from milk $P_4$ concentrations on these days, together with Milk $P_4$ measurements on Day 24 post AI.

Furthermore, milk $P_4$ data on Day 5 were exclusively used to determine the extent of luteal $P_4$ insufficiency post AI and to evaluate its impact on pregnancy rate.

Study II

A subset of the data including 987 inseminations in 795 animals, was used to identify animals with luteal insufficiency, five days post AI, for potential $P_4$ therapy, i.e to produce useful $P_4$ levels. In order to attain a timely $P_4$ supplementation, animals found on the morning of Day 5 post AI with luteal $P_4$ insufficiency were treated with CIDR (contain 1.9 g) progesterone, InterAg, Hamilton, New Zealand) in the afternoon with the device left in the vagina for a period of seven days. Consequently, animals in four commercial herds were used. For the speed of assaying milk $P_4$ concentrations and timely treatment, milk samples from three farms were assayed in our laboratory. In the fourth farm, the assay. was carried out in a separate facility but duplicates of milk samples from this farm were re-assayed subsequently in our laboratory. For the consistency of assay techniques, all statistical analyses were performed on milk $P_4$ concentrations as determined in our laboratory. A total of 91 animals identified as having $P_4$ luteal insufficiency were treated with CIDR and their pregnancy rates were compared with (156) control animals of similar milk $P_4$ levels on Day 5 pos AI.

Statistical Analysis

Regression of milk $P_4$ concentrations on Days 0, 5 and 24 on pregnancy rates were fitted using Curve expert 1.3 (Microsoft). Logistic regression analysis was used (SPSS, Windows, V.8 (SPSS, Inc.) to calculate the combined effects of milk $P_4$ concentrations on Days 0 and 5 on pregnancy rates and in characterizing the effects of parity on the incidence of luteal $P_4$ insufficiency. The effect of CIDR treatment on pregnancy rates was compared with the control untreated group using chi-square analysis. Differences in mean interval were compared using a Student t-test.

Results

Preliminary Study

From analysing daily milk $P_4$ data of 500 cycles in untreated cows raised on the University Research Fa pregnant (n=66) and non-pregnant (n=58) animals inseminated at similar intervals following regression of the CL were compared. The results are shown in Table 1:

TABLE 1

The use of daily milk sampling to determine the time of $P_4$ rise after insemination in pregnant and non pregnant animals. Oestrous cycles (n = 124) were normalised so that Day 0 is the day of CL regression.

| Parameter | Pregnant (66) Mean ± s.e. | Non-pregnant (58) Mean ± s.e. |
| --- | --- | --- |
| Days to AI after CL regression | 1.90 ± 0.13 | 1.94 ± 0.2 |
| Days from AI to $P_4$ rise >3 ng/ml | 4.08 ± 0.16[a] | 5.15 ± 0.27[b] |

[a,b]Means are different (P < 0.001)

Pregnant animals showed a significant earlier rise in milk $P_4$ concentrations (4.08±0.16 v 5.1±0.27 days, P<0.001). This emphasises the importance of adequate systemic $P_4$ levels as indicated by milk $P_4$ concentrations $\geq 3$ ng/ml as early as Day 4 post AI for normal embryo development and survival. Based on this premises, animals were distinguished as having luteal $P_4$ insufficiency if found with milk $P_4$ concentrations <3 ng/ml five days post AI (Study I) and its impact on pregnancy rate of animals above and below this level was calculated. Furthermore, in Study II the effect of $P_4$ therapy in animals thus identified as having luteal $P_4$ insufficiency post AI was investigated.

Study I
Progesterone Concentrations on Day of Insemination

The mean milk $P_4$ concentrations on Day of insemination was 1.96±0.1 ng/ml (mean ±s.e., n=1451). The CV was 199.8% indicating a high variation between animals on the day of AI. The minimum and maximum concentrations of $P_4$ were respectively, <1 and 45.6 ng/ml. As it is shown in Table 2, a total of 51.22%, 81.39% and 91.11% of inseminations were carried out when milk $P_4$ concentrations were below 1, 2 or 3 ng/ml, respectively. Although some pregnancies occurred in animals at all levels, there was a significant drop in pregnancy rate at milk $P_4$ concentrations of ±2 ng/ml.

TABLE 2

Frequency distribution of milk $P_4$ concentrations on Day of insemination and its impact on pregnancy rate (n = 1451).

| $P_4$ concentrations on Day of AI (ng/ml) | Frequency no. (%) | Pregnancy (%) |
|---|---|---|
| <1 | 645 (44.45) | 51.22$^a$ |
| 1 to 1.99 | 535 (36.87) | 45.49$^a$ |
| 2 to 2.99 | 142 (9.79) | 48.48$^a$ |
| 3 to 3.99 | 40 (2.76) | 35.89$^b$ |
| 4 to 4.99 | 15 (1.03) | 33.33$^b$ |
| 5 | 74 (5.10) | 11.29$^c$ |
| Total | 1451 (100) | 46.35 |

$^{a,b}P < 0.05$
$^{b,c}P < 0.025$
$^{a,c}P < 0.001$.

TABLE 3

The incidence of high milk $P_4$ concentrations (>3 ng/ml) on Day of AI in Holstein-Friesian cows in seven commercial herds with variable pregnancy rates (n = 1451)

| Herd | Frequency (no.) | Mean $P_4$ ± s.e. on Day 0 (ng/ml) | Frequency with Day 0 >3 ng/ml | Pregnancy |
|---|---|---|---|---|
| A† | 57 | 1.32 ± 0.19 | 3 (5.26)$^1$ | 30.77$^a$ |
| B‡ | 248 | 2.19 ± 0.17 | 49 (19.76)$^3$ | 36.60$^a$ |
| C‡ | 560 | 2.51 ± 0.21 | 53 (9.46)$^2$ | 43.88$^a$ |
| D | 26 | 1.35 ± 0.33 | 1 (3.85)$^1$ | 46.15$^a$ |
| E | 225 | 2.17 ± 0.18 | 7 (3.1)$^1$ | 48.58$^b$ |
| F | 59 | 0.96 ± 0.07 | 0 (0.0)$^1$ | 53.57$^{b1}$ |
| G | 276 | 1.35 ± 0.16 | 14 (5.07)$^1$ | 60.08$^c$ |
| Total | 1,451 | 1.96 ± 0.1 | 129 (8.9) | 46.35 |

$^{a,b,b1}P < 0.05$
$^{a,c}P < 0.001$
$^{b,c}P < 0.01$
$^{b1,c}$(NS)
$^{1,2}P < 0.01$
$^{1,3}P < 0.0001$
$^{2,3}P < 0.001$
†Animals in this herd were inseminated at the appropriate time in relation to ovulation but the low pregnancy rate may be attributed to a high incidence of embryo mortality.
‡For explanation of lower pregnancy rates see Table 5 and text.

When the data was separably analysed for each farm (Table 3), a significant difference between f was observed in the incidence of Day 0 concentrations >3 ng/ml. Generally, herds with a lower incidence of high milk $P_4$ concentrations on the Day 0 have significantly higher pregnancy rates.

Progesterone Concentrations on Day 5 Post Insemination

A total of 1451 observations of $P_4$ concentrations on Day 5 post AI were analysed. The average concentration was 5.93±0.1 ng/ml (mean±s.e.) and a CV of 66.91%, ranging from a minimum of <1 ng/ml to a maximum of 35.9 ng/ml. The frequency distribution and pregnancy rates are shown in Table 4.

TABLE 4

Frequency distribution and pregnancy rate in animals with regard to milk $P_4$ concentrations on Day 5 post insemination (n = 1451).

| $P_4$ on Day 5 post AI (ng/ml) | Frequency (no) | Frequency (%) | Pregnancy |
|---|---|---|---|
| <1 | 44 | 3.03 | 6.82$^a$ |
| 2 to 1.99 | 70 | 4.82 | 27.69$^b$ |
| 2 to 2.99 | 142 | 9.79 | 40.70$^b$ |
| 3 to 3.99 | 215 | 14.8 | 48.50$^c$ |
| 4 to 4.99 | 225 | 15.5 | 50.90$^c$ |
| 5 to 5.99 | 206 | 14.2 | 53.37$^c$ |
| 6 to 6.99 | 142 | 9.79 | 56.10$^c$ |
| 7 to 7.99 | 122 | 8.41 | 56.90$^c$ |
| 8 to 8.99 | 71 | 4.89 | 50.70$^c$ |
| >9 | 214 | 14.7 | 36.10$^b$ |
| Total | 1451 | 100 | 46.4 |

$^{a,b}P < 0.01$
$^{a,c}P < 0.0001$
$^{b,c}P < 0.01$

Figure 3:
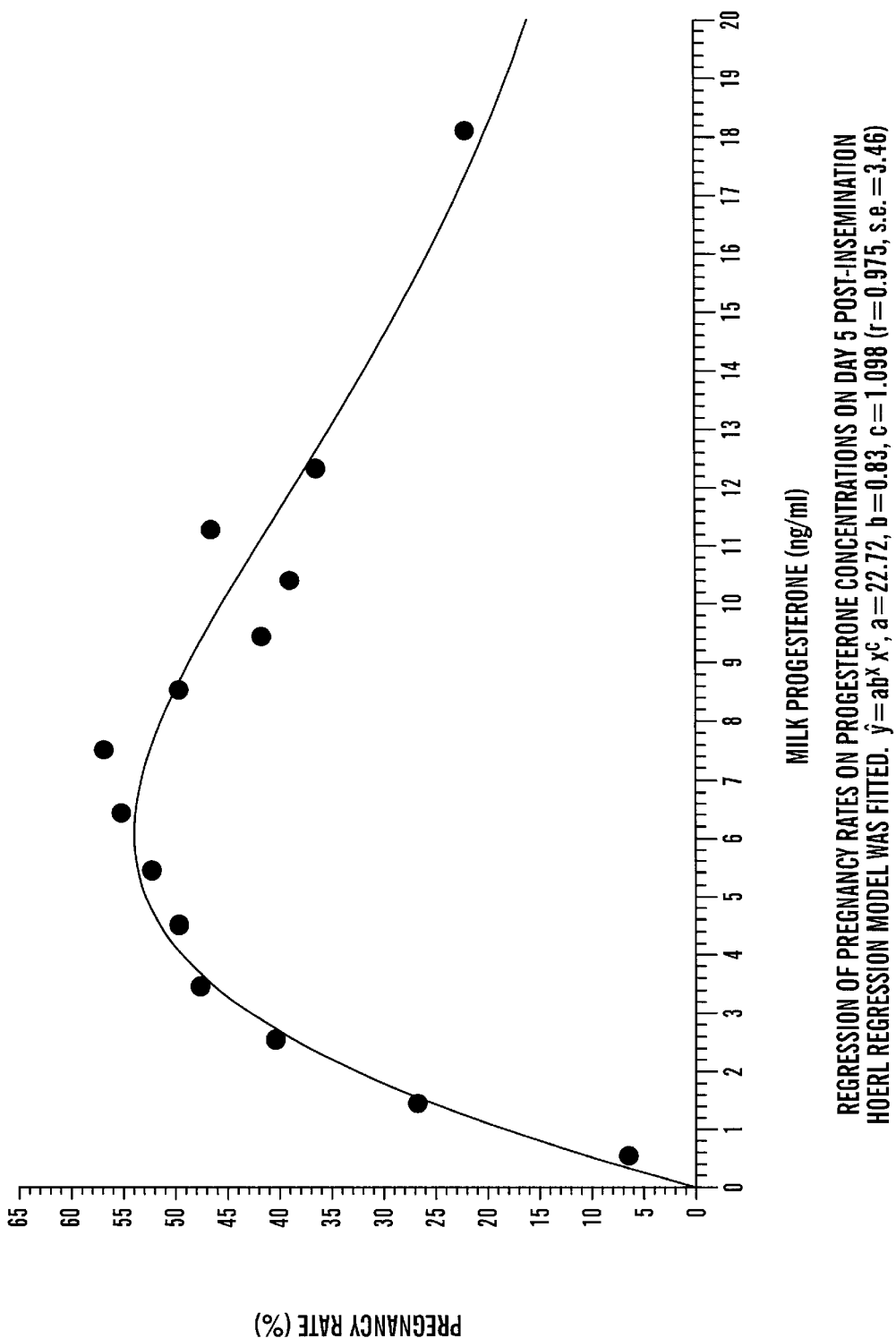
FIG. 3 illustrates a regression pregnancy rate on progesterone concentrations on Day 5 post-insemination.

Logistic regression analysis showed that the highest pregnancy rate (P<0.001) was found in animals with concentrations on Day 5 between 3 to 9 ng/ml across all milk $P_4$ concentrations on the day of AI. FIG. 3 shows the fitting of Hoerl (from Curve Expert 1.3 (Microsoft)) regression model to the association between milk $P_4$ concentrations on Day 5 and pregnancy rates.

The Use of Milk $P_4$ Concentrations on Day 5 Post AI to Verify the Day of Cycle when Untimely AI was Performed As shown in Table 5, the high milk $P_4$ concentrations on Day 0, observed in 129 animals (8.9%) tabulated in Table 2, were classified into 3 categories based on Day 5 milk $P_4$ concentrations. Animals in category B (3.5 1%) appear to have a transient $P_4$ rise on the day of AI while those in category A (1.93%) and C (3.45%) were identified as being inseminated too early or too late, respectively, in relation to ovulation.

TABLE 5

Characterizing types of untimely insemination using milk $P_4$ concentrations on Days 0 and 5 post AI.

| Group | Mean $P_4$ on Day 0(n) | Mean $P_4$ on Day 5(n) | Pregnancy rate (%) |
|---|---|---|---|
| A | 13.58 (28) | 1.65 (28) | 14.8 |
| B | 5.63 (51) | 5.32 (51) | 30.0 |
| C | 14.41 (50) | 17.8 (50) | 17.95 |

The pregnancy rates are not significantly different.

The Incidence of Luteal $P_4$ Insufficiency

To estimate the incidence of luteal $P_4$ insufficiency on Day 5 post AI, all observations (n=1650) were used regardless of whether the animal was treated or whether milk $P_4$ concentrations on Days 0 and 24 were missing. Consequently, a total of 339 (20.55%) inseminations were followed five days later by luteal $P_4$ insufficiency (<3 ng/ml). Regression analysis showed a significant positive association (P<0.001) between parity and the occurrence of insufficient $P_4$ luteal activity. The incidence is lowest in primiparous cows but continues to increase to peak after the third parity.

TABLE 6

The impact of parity (lactation number) on the incidence of luteal insufficiency ($P_4$ on Day 5 post AI <3 ng/ml) in postpartum Holstein-Friesian cows (n = 1618)

| Lactation (No.) | Frequency (No.) | Luteal insufficiency (%) |
|---|---|---|
| 1 | 570 | 10.18[a] |
| 2 | 381 | 20.73[b] |
| 3 | 248 | 29.84[c] |
| 4 | 209 | 27.75[c] |
| ≧5 | 210 | 29.52[c] |
| Total | 1618‡ | 20.55 |

‡Including all treated and untreated animals.
[a,b]P < 0.001)
[b,c]P < 0.0.01
[a,c]P < 0.0005

Pregnancy Rates in Relation to the Combined Effect of Day 0 and Day 5 Post AI Milk $P_4$ Concentrations Table 7 tabulates pregnancy rates in relation to the combined effects of various concentrations of milk $P_4$ on Days 0 and Day 5 post AI. Since animals with >3 ng/ml on Day 0 (possibly indicating untimely insemination) were excluded from the analysis, there were no significant differences between column in pregnancy rates in animals having milk $P_4$ concentrations of <1 to <3 ng/ml. However, there were differences between rows with the lowest pregnancy rates in animals with milk $P_4$ concentrations <1 ng/ml on Day 5 post AI regardless of milk $P_4$ concentrations on Day 0. The highest pregnancy rate (73.68%) was observed in animals having mean milk $P_4$ concentrations of <3 on Day 0 and 6 to 6.99 ng /ml on Day 5 post AI.

Progesterone Concentrations on Day 24 Post AI

The frequency distribution of milk $P_4$ concentrations on Day 24 post AI is tabulated in Table 8.

TABLE 8

Pregnancy rates in relation to milk $P_4$ concentrations on Day 24 post-AI (n = 1370).

| $P_4$ on Day 24 post -AI (ng/ml) | Frequency no. | (%) | Pregnant (no.) | Pregnancy rate (%) |
|---|---|---|---|---|
| <8 | 507 | (37.01) | 1* | 0.2.2[a] |
| 8 to 11.99 | 27 | (1.97) | 6 | 22.2[a] |
| 12 to 15.99 | 86 | (6.28) | 50 | 58.14[b] |
| 16 to 19.99 | 167 | (12.19) | 124 | 74.25[c] |
| 20 to 23.99 | 228 | (16.64) | 177 | 77.63[c] |
| 24 to 27.99 | 153 | (11.17) | 115 | 75.16[c] |
| 28 to 31.99 | 92 | (6.72) | 73 | 79.35[c] |
| 32 to 35.99 | 50 | (3.65) | 36 | 72.00[c] |
| 36 to 39.99 | 33 | (2.41) | 29 | 87.88[c] |
| m 40 | 27 | (1.97) | 24 | 88.89[c] |
| Total | 1370 | (100) | 635 | 46.35 |

[a,b]P < 0.001
[b,c]P < 0.01
[a,c]P < 0.0001
*One pregnant animal had $P_4$ concentration of 7.13 ng/ml on Day 24 post-AI.

The $P_4$ concentration was 15.98±0.32 ng/ml (meat±s.e., n=1451) ranging between <1 to 66.4 ng/ml. Although the minimum milk $P_4$ concentration observed in pregnant animals was 7.13 ng/ml, $P_4$ concentrations >16 ng/ml are essential for a meaningful pregnancy rate prediction. The pregnancy rate in animals with >16 ng/ml was significantly higher than those with 8 to 11.99, (P<0.001) or 12 to 15.99 ng/ml (P<0.01).

TABLE 7

Pregnancy rates in relation to milk $P_4$ concentrations on Day 0 and Day 5 post insemination

| $P_4$ concentrations on Day 5 (ng/ml) | Pregnancy rates (%) $P_4$ concentrations on Day 0 (ng/ml) | | | |
|---|---|---|---|---|
| | Up to 1 (n) | 1 to 1.99 | 2 to 2.99 | Rows |
| <1 | 9.09 (22) | 7.69 (13) | — | 8.57 (35)[a] |
| 1 to 1.99 | 38.71 (31) | 20.83 (24) | — | 30.91 (55)[b] |
| 2 to 2.99 | 43.24 (74) | 50.00 (38) | 0.09 (11) | 42.28 (123)[b] |
| 3 to 3.99 | 56.88 (109) | 37.89 (66) | 53.30 (15) | 50.00 (182)[c] |
| 4 to 4.99 | 56.38 (94) | 46.99 (83) | 45.83 (24) | 51.24 (201)[c] |
| 5 to 5.99 | 53.50 (86) | 54.32 (81) | 64.71 (17) | 57.29 (184)[c] |
| 6 to 6.99 | 49.06 (53) | 60.70 (61) | 73.68 (19) | 57.25 (133)[c] |
| 7 to 7.99 | 68.89 (45) | 47.97 (48) | 60.00 (15) | 59.09 (108)[c] |
| 8 to 8.99 | 54.29 (35) | 46.43 (28) | 66.67 (6) | 52.17 (69)[c] |
| 9 to 9.99 | 43.48 (23) | 41.67 (24) | 28.62 (7) | 39.29 (54)[b] |
| Columns | 51.22[NS] | 46.40[NS] | 52.6[NS] | 49.76 |

[a,b]P < 0.05
[b,c]P < 0.01
[a,c]P < 0.001
[NS]The difference between means of columns was not significant.

Figure 4:
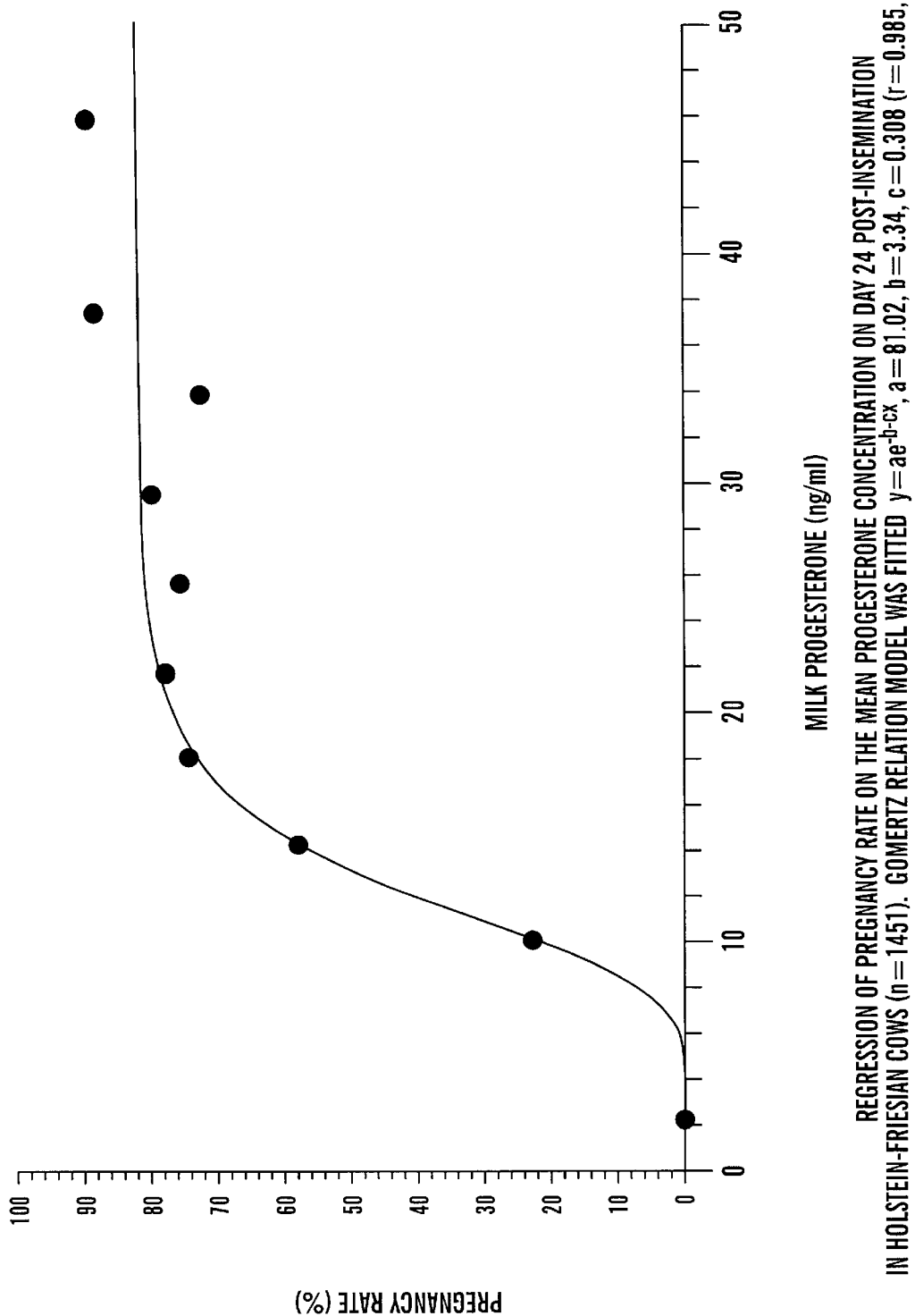
FIG. 4 illustrates a regression pregnancy rate on progesterone concentrations on Day 24 post-insemination.

A Gomertz relation model (Microsoft Curve Expert 1.36) was fitted to pregnancy rates and the mean milk $P_4$ concentrations on Day 24 post AI per group. The results of this analysis is shown in FIG. 4.

Accuracy of Predicting pregnancy Using Milk $P_4$ Concentrations of Days 0, 5 and 24 Post AI Out of 1370 cows with known pregnancy status, a total of 635 (46.35%) were identified as being pregnant. The accuracy of predicting pregnancy using $P_4$ concentrations on Days 0, 5 and 24 in 750 cows with Day 24 $P_4$ values above 16 ng/ml is shown in Table 9. The highest accuracy was in animals having $P_4$ concentrations on Day 5 between 3 to 9 ng/ml (Groups B and E) while the lowest was in animals apparently inseminated at an inappropriate time in relation to ovulation (Groups D and F).

TABLE 9

Predicting pregnancy using milk $P_4$ concentrations on Days 0, 5 and 24. All animals had $P_4$ concentrations >16 ng/ml on Day 24 Post AI and later confirmed pregnancy status (n = 750).

| Group | Observations (no.) Total | Pregnant | Mean $P_4$ (ng/ml) Day 0† | Day 5‡ | Pregnancy rate (%) |
|---|---|---|---|---|---|
| A | 82 | 56 | 0.9 | 2.07 | 68.29[b] |
| B | 529 | 440 | 1.10 | 5.51 | 83.18[a] |
| C | 85 | 58 | 1.15 | 11.55 | 68.24[b] |
| D | 12 | 4 | 6.91 | 1.82 | 33.33[c] |
| E | 20 | 14 | 6.24 | 5.17 | 70.00[a] |
| F | 22 | 6 | 15.86 | 18.35 | 27.27[c] |

†Animals were grouped in two categories of <3 ng/ml (A to C) or >3 ng/ml (D to F) on Day 0 post-AI.
‡Animals were grouped into <3, (A and D), ≧3 to <9 (B and E) and >9 ng/ml (C and F) on Day 5 post-AI.
[a,b] and [b,c] differ (P < 0.01)
[a,c] (P < 0.0005).

Study I

A subset of the milk $P_4$ data covering 987 observations from 795 cows in four commercial herds was analysed. The samples were assayed on the day of sample collection. Animals found with luteal insufficiency ($P_4$<3 ng/ml) in the morning of Day 5 post AI were supplemented in the afternoon with exogenous progesterone using a CIDR (produced by Interag, Hamilton, New Zealand; MacMillan K. L. and A J. Peterson. (1993). Anim. Reprod. Sci. 33: 1–25, MacMillan K. L. et al. (1991) Anim. Reprod. Sci. 26: 2540).

Pregnancy rates with regard to the magnitude of progesterone on Day 5 post AI and the effects of treatment with CIDR are shown in Table 10.

| Mean $P_4$ on Day 5 post AI (ng/ml) | Untreated (no.) | Pregnancy (%) | Treated (no.) | Pregnancy (%) |
|---|---|---|---|---|
| <1 | 30 | 10 | 13 | 15.38 |
| 1 to 1.99 | 44 | 28.95[a] | 19 | 89[b] |
| 2 to 2.99 | 82 | 41.77 | 31 | 37.93 |
| 3 to 3.99 | 115 | 49.55 | 12 | 50 |
| 4 to 4.99 | 129 | 50.81 | 9 | 55.56 |
| 5 to 5.99 | 125 | 51.18 | n/d* | n/d |
| 6 to 6.99 | 78 | 59.21 | n/d | n/d |
| 7 to 7.99 | 101 | 65 | n/d | n/d |
| 8 to 8.99 | 48 | 48.89 | n/d | n/d |
| >9 | 144 | 39.52 | n/d | n/d |
| All cows with milk $P_4$ <3 ng/ml on Day 5 post AI | | 31.97[a] | 63 | 39.34 |

*"n/d" = No data

Table 10 Pregnancy rates in treated and untreated control animals in relation to milk $P_4$ concentrations on Day 5 post-AI.

The lowest pregnancy rates were in both control and treated animals having milk $P_4$ concentrations on Day 5 <1 ng/ml (average 0.5 ng/ml). Treatment with CIDR significantly (P<0.05) increased pregnancy rates in animals having $P_4$ concentrations between 1 to 1.99 (mean 1.5 ng/ml). The highest pregnancy rate was in animals with a spontaneous rise in $P_4$ concentrations on Day 5 to between 4 to 8 ng/ml (average 4.5 to 7.5 ng/ml).

Although the treatment protocol was designed to treat animals with low $P_4$ concentrations on Day 5 post AI, milk samples from 28 animals, previously assayed elsewhere, were re-assayed in our laboratory and found with $P_4$ concentrations 23 ng/ml. There was no treatment effect on pregnancy rate in these animals as shown in Table 10.

Milk progesterone determinations in the dairy cow offer an accurate, objective and non-invasive means of studying the hormone status of individual cows and investigating whether ovulation and insemination have occurred at the correct time by examination of the luteinization rate (timing and rate of $P_4$ rise). Furthermore, it can assist in the early diagnosis of pregnancy. Following the regression of the corpus luteum, oestrous and insemination typically occur during the inter-luteal interval when milk $P_4$ concentrations are usually lower than 3 ng/ml. This should then be followed 4 days post ovulation by measurable luteinzation as indicated by increasing milk $P_4$ concentrations. In the present study, a protocol was implemented with the aim of quantifying the incidence of untimely insemination and luteal insufficiency and their impact on pregnancy rates in Holstein-Friesian cows. An additional objective was to study the effects on pregnancy rates of supplementing $P_4$ in animals identified with luteal $P_4$ insufficiency.

In the preliminary study, as shown in Table 1, pregnant and non pregnant animals were inseminated at equal intervals following regression of the CL, but differed in luteinization rates with a delay of one day in the availability of adequate $P_4$ having a detrimental effect on pregnancy. This could be due to a delayed ovulation of an abnormal follicle or the development of an incompetent CL.

Delayed ovulation in relation to oestrous has been previously reported in cows using ultrasound scan and heat mount detectors (Walker, W. L. et al (1996) J. Dairy. Sci. 79: 1555–1561) and the ovulation of a persistent follicle was found by Ahmad et al. (Ahmad N. et al (1996) J. Anim. Sci. 74: 1943–1952) to be followed by a delayed rise in $P_4$ concentrations after oestrous when compared to ovulation of a growing follicle. Furthermore, Shelton et al. (Shelton, K. et al (1990) J. Reprod. Fertil. 90: 1–10) demonstrated a significant difference in the period between the preovulatory LH peak and the post ovulation progesterone rise in older subfertile cows compared with fertile heifers. Therefore a lower pregnancy rate may be attributed to either fertilization failure following a delayed ovulation or to retarded embryo growth due to $P_4$ insufficiency.

Following analysis of the results of the preliminary study, Study I was carried out to quantify the effects of subsequent luteinization rate on pregnancy in animals inseminated at the appropriate time.

Timely Insemination: Milk $P_4$ Concentrations on Day of Insemination

In this study, luteinization is empirically defined as the presence of milk $P_4$ concentrations which are ≦3 ng/ml. In consequence, animals found with milk $P_4$ concentrations ≦3 ng/ml on Day 0 may be initially classified as being inseminated at an inappropriate time in relation to ovulation. From the results shown in Table 2, a high proportion (91.1%) of animals had milk $P_4$ concentrations on Day 0 between 0 to <3 ng/ml. The remaining 8.9% of animals had levels above 3 ng/ml and might be tentatively identified as being inseminated during late or early luteal activity of an oestrous cycle. Although some pregnancies were detected in all groups, it was highest in animals with milk $P_4$ concentrations <3 ng/ml and lowest in those with $P_4 \geq 5$ ng/ml.

Herd effects on the incidence of high milk $P_4$ concentrations on the day of AI are shown in Table 3. This ranged from 0% in one herd to a high of 19.8% in another.

Differences between herds may be attributed in part to some cows showing a transient rise of progesterone (3.95% in this study) or to high levels indicative of untimely insemination. Milk $P_4$ concentrations >3 ng/ml on the day of insemination in otherwise fertile animals (an atypical blip) have previously been reported by Bulman and Lamming (7). These authors also reported data from one herd showing a 49% incidence of high levels >3 ng/ml on the day of insemination.

The pregnancy rates were lowest in herds with >5% of animals showing a high progesterone concentration on the day of insemination. However since other factors may also be involved in the establishment or failure of a pregnancy, caution must be exercised before classifying an insemination as being untimely; based solely on a particular milk $P_4$ concentration. It is clear that some animals with high milk $P_4$ levels on Day 0 become pregnant (Table 5). Additional information is needed to validate whether an AI is being cared out an inappropriate time. The high milk progesterone concentrations in some herds could be influenced by the time of milk sampling in relation to insemination or result from stress imposed in particular herds by segregating animals away from herd mates pending the insemination procedure.

Milk Progesterone Concentrations on Day 5 Post AI

From the results of the preliminary study, Day 4 post AI was considered as the critical period when the availability of adequate $P_4$ is essential for a higher pregnancy rate. Based on this, the sampling protocol included, in addition to the day of insemination, a milk sample taken on Day 5 post AI for all animals studied It was assumed that $P_4$ insufficiency by this day signals a clear risk of compromising embryo survival.

As it is shown in Table 4, the variation of progesterone concentrations on Day 5 following insemination potentially indicates a highly variable luteinization rate between cows. Since progesterone plays a major role in controlling the uterine secretion of nutrients essential for the embryonic growth and development (Geisert R. D et al (1992) Reprod. Fertil. Dev. 4: 301–305); delayed luteinization is known to have detrimental effects on pregnancy rates (Ahmad, N et al (1996) J. Anim. Sci. 74: 1943–1952; Lamming, G. E and A. O Darwash (1995) Biol. of Reprod. 52: Suppl. 1, abstr. 63). This was also confirmed by the data presented in Table 4 where the lowest pregnancy rate was found in animals with luteal progesterone insufficiency ($P_4$<3 ng/ml), while the highest pregnancy rates were observed in animals having adequate milk $P_4$ concentrations from >3 ng/ml to 9 ng/ml (See also FIG. 3). Interestingly, higher $P_4$ levels (>9 ng/ml) on Day 5 post AI was found to be associated with a lower pregnancy rate, which may be due to this group containing cows with a delayed insemination in relation to ovulation.

A delayed progesterone rise post ovulation has been shown to be implicated as a cause of subfertility. Shelton et al (Shelton, K et al (1990) J. Reprod. Feril. 90: 1–10) in studying the interval between the preovulatory LH surge and a plasma $P_4$ level >1 ng/ml in older subfertile cows compared to more fertile pregnant and cyclic heifers, showed a significant delay in the post ovulatory progesterone rise and a lower rate of rise in the older cows. This indicated a possible association between luteal $P_4$ insufficiency and the lower pregnancy rates in older animals.

As shown in Table 6, the incidence of luteal insufficiency was positively associated with parity, increasing from 10.18% during the first lactation to 29.84% by the third lactation. It is not clear from the present study how parity affects the incidence of luteal P4 insufficiency in lactating dairy cows or whether the trait is heritable. In this regard, Darwash et al. (Darwash A O et al (1998) Fertil and Reprod. Grub, Germany, November 1997) have estimated the repeatability of prolonged inter-luteal intervals within a lactation in British Friesian cows to be r=0.094 (P<0.01).

Progesterone concentrations on Day 5 may also be effectively used to verify the types of untimely insemination, previously described in 8.9% of animals (Table 2). As it is shown in Table 5, animals in group A (1.93%) may be classified as being inseminated too early (near or before the time of CL regression) while those in Group C (3.51%) appear to have been inseminated too late in relation to ovulation (i.e. during a luteal phase). In a parallel study, subsequent monitoring of 26 animals in group C confirmed that the inseminations were performed during the luteal phase (Royal, M. D., 1999, Personal communication). This implies that 3.95% of animals (group B) have an authentic transient milk $P_4$ rise on the day of insemination.

The optimum milk $P_4$ concentrations on Days 0 and 5 for high pregnancy rates are tabulated in Table 7. Maximum pregnancy rates of 73.68% and 68.89% were observed in a group of animals with milk $P_4$ concentrations on Day 0 of <3ng/ml and 6 to 7.99 ng/ml on Day 5 post AI. Therefore if $P_4$ supplementation is deemed necessary the treatment protocol selected should achieve a milk $P_4$ concentration of 5–8 ng/ml by Day 5 post AI.

Day 24 Milk $P_4$ Concentrations and Pregnancy Rate

Data from this study (Table 8, FIG. 4) show that the critical level required is >16 ng/ml, since pregnancy rates significantly increased to this level. Using this information, it was then possible to combine values on Days 0, 5 and 24 to confirm (Table 9) that the highest pregnancy rates occur in animals with Day 0 values below 3 ng/ml, with Day 5 values between 3 and 9 ng/ml, and Day 24 values of >16 ng/ml. The significantly higher pregnancy rate achieved in the large number of cows (n=529) in Group B, which embodies these criteria, indicates the importance of achieving this pattern for optimum fertility. A significantly (P<0.01) lower pregnancy rate was observed in animals with untimely insemination in relation to ovulation (Groups D and F). The $P_4$ concentration of 16 ng/ml found in the present study for highest accuracy is substantially higher than the 6.50 ng/ml concentrations advocated by Booth and Holdsworth (Booth, J. M and R. J. Holdsworth (1976) Br. Vet. J. 132: 518–533) to differentiate on Day 24 between negative and positive pregnancy results.

Progesterone Supplementation

In study II, a novel approach was adopted to assess whether $P_4$ supplementation (using CIDR) could improve pregnancy rate. In the present study, contrary to past practices of blanket treatment (Robinson, N. A. et al (1989) J. Dairy Sci. 72: 202–207; Macmillan, K. L. and A. J. Peterson (1993) Anim. Reprod. Sci. 33: 1–25) animals identified as having insufficient luteal $P_4$ on Day 5 post AI were targeted for $P_4$ supplementation. The choice of CIDR was natural since it has been used successfully to increase pregnancy rates when given on Days 4 to 9 post insemination (Macmillian K. L. and A. J. Peterson 1993) Anim. Reprod.

Sci. 33: 1–25) and because the rate of absorption has been determined Treatment of four ovariectomized lactating Holstein cows with CIDR raised milk $P_4$ concentrations to a maximum of 8.8±0.98 ng/ml on Day 2 post treatment (Van Cleeff, J et al (1992) Anim. Reprod. Sci 27: 91–106). In a parallel study (Darwash A. O. et al (1999b) Anim. Sci. (in press)) using intact Holstein-Friesian cows, CIDR treatment on Day 2 post oestrous, raised milk $P_4$ concentrations from a mean of 1.35±46 ng/ml to 8.84±1.11 ng/ml, on Day 3 post oestmous, in 10 control and 10 treated animals respectively. The present study aimed to ensure that 3 to 9 ng/ml of milk $P_4$, as found in study I associated with a high pregnancy rate, was achieved by Day 5 post AI. Supplementation of $P_4$ on Day 5 rather than on Day 4 post AI was selected to ensure that the treated animals were clearly identified with insufficient progesterone. Furthermore, progesterone treatment during early met-oestrus may have compromised CL lifespan (Garrett, J. E. et al (1988) Prostaglandins 36: 85–96) or interfered with the speed of zygote passage through the oviduct El--khan, M. M. and D. E. Noakes (1989) Br. Vet J. 145: 328–336; Ruckeebusch, Y and F. Bayard (1975) J. Reprod. Fertil. 43: 23–32). In the present study, it was possible to verify whether exogenous $P_4$ is beneficial and if so at what endogenous $P_4$ magnitude.

Knowledge of millk $P_4$ concentrations prior to treatment clarified a number of issues. It showed that in animals having $P_4$<1 ng/ml, the pregnancy rate was lowest and that treatment did not produce a significant improvement over that of the control (15.38% vs 10.0%). This may be attributed to either an acute delay in ovulation in some cows which may have reduced fertilization rate, or to cases where embryo development was already compromised, thus making adequate $P_4$ concentrations through supplementation which was ineffective to improve pregnancy rates.

However, in animals with fertilized ova but followed by a reduced luteinization rate, the treatment significantly improved pregnancy rate, probably through a higher rate of embryo survival. These may be similar to those subfertlle cows identified by Shelton et al, (Shelton, K. et al (1990) J. Reprod. Fertil. 90: 1–10) as having delayed luteinization in relation to the pre-ovulatory LH peaks and a lower rate of progesterone secretion. Provided that adequate endogenous $P_4$ levels are available on Day 5 post AI additional exogenous $P_4$ is not required. Progesterone supplementation will be effective if it is given to animals with luteal insufficiency but not with acute delayed ovulation. Thus the variation between animals in $P_4$ concentrations on day of treatment way have contributed to previous inconsistency in pregnancy rates observed in animals supplemented with progesterone using CIDR (Macmillan, K. L. and A. J. Peterson (1993) Anim. Reprod. Sci. 33: 1–25; Van Cleeff, J. et al (1996) Theriogenology 46: 1117–1130) or PRID (Robinson, N. A. et al (1989) J. Dairy Sci. 72: 202–207).

However, the finding in this study that improvement in pregnancy rate following $P_4$ supplementation of cows with >3 ng/ml on Day 5 post AI was limited to those with values between 1 and 2 ng/ml was unexpected and requires scrutiny. From the results of Study I, increased pregnancy rates occurred in untreated animals with Day 5 $P_4$ concentrations between 3 to 9 ng/ml milk. Therefore, it would be expected that improvement due to $P_4$ supplementation should also have occurred in the treated group with pretreatment milk $P_4$ concentrations of 2 to 3 ng/ml, but treatment was without effect. Unfortunately, information is lacking concerning the changes in $P_4$ concentrations of animals immediately after the insertion of CIDR. It is therefore possible that the treatment schedule for these animals did not produce a pattern of $P_4$ absorption and metabolism which simulated that occurring naturally where $P_4$ concentrations develop gradually. Equally, it is possible that the CIDR with the $P_4$ content used, in animals inseminated at the appropriate time, may have elevated $P_4$ concentrations above 9 ng/ml, at which in Study I some depression of pregnancy rate occurred (See Table 7 and FIG. 3). Attention should be given to the possibility that the higher levels of $P_4$ created may have inhibited uterine receptor development. Further studies are therefore required to determine the effects of the CIDR used on $P_4$ levels and whether a device with a lower rate of $P_4$ release would have improved the pregnancy rate of this group of animals, possibly by insertion as early as Day 3 to 4 post AI.

The maximum pregnancy rate in relation to endogenous $P_4$ concentrations was approximately 60% (Table 7). There seems to be an underlying embryo loss of approximately 30% unrelated to endogenous $P_4$ concentration and its known effects on embryo development and secretion of interferon-J. In this respect, Thatcher et al. (Thatcher W. W et al (1995) J. Reprod. Fert. Suppl. 49: 15–28), postulated that the inadequate response of the cow to embryonic interferon-J, may account for 20% of the embryo loss in cattle. Further investigations are needed to characterize the variation between animals in their sensitivity to embryonic antiluteolytic signals.

The $P_4$ concentrations in milk on Day 5 post AI may be effectively used to distinguish untimely insemination and luteal $P_4$ insufficiency. As shown in Table 4 and FIG. 3, it may also be used as an early test for non-pregnancy with 70% accuracy (only 30% cows with milk $P_4$<3 ng/ml were pregnant).

Analysis of daily milk samples from dairy cows showed that an early rise in milk $P_4$ concentrations >3 ng/ml by Day 4 post insemination (AI) is necessary to achieve a high pregnancy rate. Milk $P_4$ concentrations on the day of AI (Day 0) and Days 5 and 24 thereafter, were used to quantify the incidence of untimely AI and to assess luteal $P_4$ sufficiency in early pregnancy and the accuracy of detecting pregnancy.

The highest pregnancy rates occurred in animals with milk $P_4$ concentrations <3 ng/ml on Day 0, 6 to 9 ng/ml on Day 5 and >16 ng/ml on Day 24. Cows with <3 ng/ml on Day 5 (20.55%) judged to show luteal insufficiency had a significantly lower pregnancy rate. Parity had a significant effect on the incidence of luteal $P_4$ insufficiency, with 10.2% in primiparous cows rising to 29.8% by the third lactation.

Analysis of milk $P_4$ concentrations on both Days 0 and 5 post AI is necessary to distinguish the correct timing of AI and the accuracy of predicting pregnancy. Low $P_4$ concentrations on Day 5 (<3 ng/ml) signals the likelihood of non-pregnancy. Supplementing $P_4$ on Day 5 post AI in animals identified as having insufficient luteal $P_4$ was effective in improving pregnancy rates when milk $P_4$ concentrations were between 1 to 2 ng/ml but not in animals above or below this range.

What is claimed is:

1. A method of improving the probability of pregnancy success in cows, comprising:
   a) measuring milk progesterone levels from a cow on Day 4, 5, or 6 post-insemination;
   b) identifying those cows with a reduced progesterone level as cows in need of progesterone supplementation, wherein a reduced progesterone level is <3 ng/ml$^{-1}$; and
   c) supplying the cows in need of progesterone supplementation with progesterone, or a functional equivalent thereof, on the day of measuring the milk progesterone levels thereby improving probability of pregnancy success.

2. The method according to claim 1 in which the levels are measured on Day 4.

3. The method according to claim 2 in which the milk progesterone levels are determined by RIA or ELISA.

4. The method according to claim 2 in which progesterone or a functional equivalent thereof is supplied to provide a milk progesterone or equivalent level of $\leq 9$ ng ml$^{-1}$.

5. The method according to claim 4 in which the milk progesterone levels are determined by RIA or ELISA.

6. The method according to claim 1 in which progesterone or a functional equivalent thereof is supplied to provide a milk progesterone or equivalent level of $\leq 9$ ng ml$^{-1}$.

7. The method according to claim 6 in which the milk progesterone levels are determined by RIA or ELISA.

8. The method according to claim 1 in which the milk progesterone levels are determined by RIA or ELISA.

9. The method according to claim 1 in which the levels are measured from Day 5.

10. The method according to claim 9 in which the progesterone or a functional equivalent thereof is supplied if the detected level of milk progesterone is between 1–1.99 ng ml$^{-1}$.

11. The method according to claim 9 in which progesterone or a functional equivalent thereof is supplied to provide a milk progesterone or equivalent level of $\leq 9$ ng ml$^{-1}$.

12. The method according to claim 9 in which the milk progesterone levels are determined by RIA or ELISA.

13. The method according to claim 1 in which the progesterone or a functional equivalent thereof is supplied if the detected level of milk progesterone is between 1–1.99 ng ml$^{-1}$.

14. The method according to claim 13 in which progesterone or a functional equivalent thereof is supplied to provide a milk progesterone or equivalent level of $\leq 9$ ng ml$^{-1}$.

15. The method according to claim 13 in which the milk progesterone levels are determined by RIA or ELISA.

\* \* \* \* \*